(12) United States Patent
Wimmer et al.

(10) Patent No.: US 11,558,951 B2
(45) Date of Patent: Jan. 17, 2023

(54) POWER SUPPLY APPARATUS FOR AN X-RAY IMAGING APPARATUS, X-RAY IMAGING APPARATUS AND ASSOCIATED METHOD

(71) Applicant: Siemens Healthcare GmbH, Erlangen (DE)

(72) Inventors: Michael Wimmer, Weisendorf (DE); Jan Berk, Hohenroda (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/469,938

(22) Filed: Sep. 9, 2021

(65) Prior Publication Data
US 2022/0086997 A1    Mar. 17, 2022

(30) Foreign Application Priority Data
Sep. 15, 2020  (DE) .................... 10 2020 211 542.7

(51) Int. Cl.
*H05G 1/54*    (2006.01)
*H05G 1/30*    (2006.01)
*A61B 6/00*    (2006.01)

(52) U.S. Cl.
CPC ............... *H05G 1/54* (2013.01); *H05G 1/30* (2013.01); *A61B 6/56* (2013.01)

(58) Field of Classification Search
CPC ....................................................... H05G 1/54
See application file for complete search history.

(56) References Cited

U.S. PATENT DOCUMENTS 3,916,251 A * 10/1975 Hernandez ............... H05G 1/34
378/110
2005/0281377 A1   12/2005 Heinze
(Continued)

FOREIGN PATENT DOCUMENTS

DE          10355424 A1    6/2005
DE       102009010219 A1    9/2010
DE       102010042565 A1    4/2012

OTHER PUBLICATIONS

German Search Report for German Patent Application No. 102020211542.7 dated Apr. 7, 2021.

*Primary Examiner* — Chih-Cheng Kao
(74) *Attorney, Agent, or Firm* — Harness, Dickey & Pierce, P.L.C.

(57) ABSTRACT

A power supply apparatus for an X-ray imaging apparatus includes grid connection device(s) to connect to a power grid providing an AC input voltage, including circuit protection arrangement(s) to not trip below a safety current; an actively actuatable transformer arrangement to transform the AC input voltage into a DC output voltage as a supply voltage for the X-ray imaging apparatus; an electrical energy storage system; and a control apparatus to actuate the transformer arrangement to limit power consumption from the electric power grid as a function of the safety current and make up for a deficiency of a power requirement for the X-ray imaging apparatus from the energy storage system. The control apparatus is configured to actuate the transformer arrangement for time-dependent limitation of power consumption from the power grid according to a current/time profile, the current/time profile being deduced from a time-based trip profile of the circuit protection arrangement.

23 Claims, 4 Drawing Sheets

(56) References Cited

U.S. PATENT DOCUMENTS

2010/0220837 A1* 9/2010 Bressel ................ A61B 6/032
 378/103
2017/0027537 A1* 2/2017 Zhang ................ A61B 6/4405
2018/0263591 A1 9/2018 Shanthakumar et al.

* cited by examiner

POWER SUPPLY APPARATUS FOR AN X-RAY IMAGING APPARATUS, X-RAY IMAGING APPARATUS AND ASSOCIATED METHOD

PRIORITY STATEMENT

The present application hereby claims priority under 35 U.S.C. § 119 to German patent application number DE 102020211542.7 filed Sep. 15, 2020, the entire contents of which are hereby incorporated herein by reference.

FIELD

Example embodiments of the invention generally relate to a power supply apparatus for an in particular medical X-ray imaging apparatus In at least one embodiment, the power supply apparatus comprises:

a grid connection device(s) for connection to a power grid providing an AC input voltage, which has at least one circuit protection arrangement which does not trip below a safety current, an actively actuatable transformer arrangement, in particular comprising a rectifier and a step-up converter, for transforming the AC input voltage into a DC output voltage as supply voltage for the X-ray imaging apparatus, an electrical energy storage system and a control apparatus for actuating the transformer arrangement to limit power consumption from the electric power grid as a function of the safety current and to make up for a deficit in power requirement for the X-ray imaging apparatus from the energy storage system.

In addition, at least one embodiment of the invention generally relates to an X-ray imaging apparatus and to a method for operating a power supply apparatus.

BACKGROUND

X-ray imaging is a long-established procedure, in particular in medical technology. X-ray imaging apparatuses (X-ray machines) have the peculiar feature of major load fluctuations in electrical power consumption. For example, in standby mode an X-ray imaging apparatus draws only a relatively small and largely constant base load from the power grid. If an X-ray is being captured, however, a very high peak load arises for a very short period, which has likewise to be delivered by the power grid. This peak load arises in order, in particular using an X-ray tube or other X-ray source component of the X-ray imaging apparatus, to generate an X-ray pulse for capturing an image.

These requirements are met in the prior art through the provision of a suitable power grid supply connection. To this end, however, the power grid often has to be adapted at the planned installation location for the X-ray imaging apparatus, for example with regard to enhanced circuit protection measures and increased line cross-sections. This entails extra effort and results in an interruption to work procedures and thus in additional costs, and may constitute an inhibitory threshold for a medical facility, for example a hospital or a doctor's practice, wishing to upgrade to a higher power X-ray machine.

This is because even with X-ray sources which require only small peak powers, for example mammography machines, a common, conventional grounding socket outlet is insufficient for operating the X-ray imaging apparatus and changes have to be made to the installation on the power grid side.

To counteract these problems, the prior art has proposed, for example, using X-ray imaging apparatus with an energy storage function, which buffers the necessary peak energy. In this case, an additional electrical energy storage system is provided in the X-ray apparatus, wherein a control apparatus ensures that a power requirement of the other components of the X-ray imaging apparatus is always met in part by the energy storage system and in part by the electric power grid if it exceeds a grid power available from the power grid. The maximum line power drawable from the power grid is conventionally limited by the control apparatus such that circuit protection measures provided on the grid side, for example a circuit protection arrangement comprising at least one circuit protection device(s), are not tripped. With regard to such circuit protection arrangements, it is known to indicate an associated safety current, which is also known as a nominal current or guaranteed minimum holding current, which ensures that the circuit protection arrangement does not trip and cap the power supply. To implement such a restriction of power consumption from the electric power grid to a specific line power, it is known, for example, to actuate an actively actuatable transformer arrangement of a corresponding power supply apparatus for the X-ray imaging apparatus such that the current in the power grid does not exceed the safety current. This intervention may be carried out, for example, as part of automatic control of the transformer arrangement, which also serves in power factor correction (PFC). Such transformer arrangements may for example take the form of a sequence of a bridge rectifier and a step-up converter or indeed a flyback converter. The relevant factor here is that an actuatable transformer topology is present. Other potential prior art solutions also proposed provide an additional, external uninterruptible power supply between the X-ray imaging apparatus and the power grid.

DE 10 2010 042 565 A1 discloses by way of example a device for supplying a medical imaging machine with electrical energy, wherein the device is designed such that the medical imaging machine can be operated solely with the normal DC voltage provided by a charging device, with normal DC voltage provided by the charging device and an energy storage system or solely with the off-grid normal DC voltage provided by the energy storage system. Lithium-ion storage batteries are used as energy storage systems, wherein the device therein is able to operate an X-ray machine using a conventional power grid supply connection without having to overload the power grid. In particular, the X-ray machine is operable using a normal three-phase 16 amp service connection, wherein 16 A is an example safety current.

DE 103 55 424 A1 describes an X-ray machine with a device(s) for storing energy which comprise an ultracapacitor for compensating deficits in the energy which can be drawn from an energy supply grid.

DE 10 2009 010 219 A1 relates to an imaging tomography machine, which uses an energy storage system to enable operation of the tomography machine without special measures using the customer's normal service connection. The power grid therefore no longer has to be adapted on the customer's premises to the maximum power required in high power operation by laying lines with a higher level of circuit protection.

In the specific field of X-ray imaging apparatus, in which peak powers have to be drawn only briefly, capacitors, in particular also supercapacitors (supercaps), are suitable as energy storage systems, since they can be rapidly charged and discharged. However, it is desirable to make these of small dimensions for reasons of cost, space and effort. Other, rapid-charging and -discharging storage technologies, for example storage batteries, are likewise costly and complex to implement.

SUMMARY

At least one embodiment of the invention enables improved utilization of the power grid in X-ray imaging apparatus and/or to allow inexpensively implemented energy storage systems.

Embodiments of the invention are directed to a power supply apparatus, an X-ray imaging apparatus and a method for operating a power supply apparatus. Advantageous developments are revealed by the claims.

In a power supply apparatus of an embodiment, the invention provides that the control apparatus for actuating the transformer arrangement for time-dependent limitation of power consumption from the power grid is configured according to a current/time profile, in particular related to a grid current flow from the power grid, wherein the current/time profile is deduced from a time-based trip profile of the circuit protection arrangement, which in particular takes account of a thermal circuit protection device(s) tripping in the event of persistent overloading.

For X-ray imaging apparatus, at least one embodiment of the present invention may be understood as a development of configurations which allow the operation of X-ray imaging apparatus even using normal service connections. It goes without saying, therefore, that this is straightforwardly possible, also in the context of at least one embodiment of the present invention, once the current or power drawn from the power grid has been throttled in such a way by the specific automatic control method that values remain below the trip characteristic of the circuit protection arrangement installed in the building wiring system. This means that the grid connection used by the grid connection device(s) of the power supply apparatus is not overloaded electrically and the power grid-side grid connection does not have to be adapted. It should be highlighted in this respect that in a particularly advantageous configuration of at least one embodiment of the present invention the current/time profile may be adaptable on the user side to various trip profiles, such that it may ultimately be selected to match the planned location for installation of the X-ray imaging apparatus. In other words, any desired current/time profile may conveniently be set.

In addition to the power supply apparatus, at least one embodiment of the present invention also relates to an X-ray imaging apparatus, having a power supply apparatus according to the present invention. All explanations with regard to the power supply apparatus according to at least one embodiment of the invention may be applied analogously to the X-ray imaging apparatus according to at least one embodiment of the invention, such that the advantages which have already been stated can also be obtained therewith.

At least one embodiment of the present invention also relates to a method for operating a power supply apparatus for an in particular medical X-ray imaging apparatus, the power supply apparatus comprising:

a grid connection device(s) for connection to a power grid providing an AC input voltage, which has at least one circuit protection arrangement which does not trip below the safety current, an actively actuatable transformer arrangement, in particular comprising a rectifier and a step-up converter, for transforming the AC input voltage into a DC output voltage as supply voltage for the X-ray imaging apparatus, an electrical energy storage system and a control apparatus for actuating the transformer arrangement to limit power consumption from the electric power grid as a function of the safety current and to make up for a deficit in power requirement for the X-ray imaging apparatus from the energy storage system, which method is distinguished in that the control apparatus actuates the transformer arrangement for time-dependent limitation of power consumption from the power grid according to a current/time profile, in particular related to a grid current flow from the power grid, wherein the current/time profile is deduced from a time-based trip profile of the circuit protection arrangement, which in particular takes account of a thermal circuit protection device(s) tripping in the event of persistent overloading.

At least one embodiment of the present invention also relates to a power supply apparatus for an X-ray imaging apparatus, the power supply apparatus comprising:

at least one grid connection device, to connect to a power grid providing an AC input voltage, including at least one circuit protection arrangement configured to not trip below a safety current;

an actively actuatable transformer arrangement to transform the AC input voltage into a DC output voltage as a supply voltage for the X-ray imaging apparatus;

an electrical energy storage system; and a control apparatus to actuate the transformer arrangement to limit power consumption from the electric power grid as a function of the safety current and to make up for a deficiency in a power requirement for the X-ray imaging apparatus from the energy storage system, the control apparatus being configured to actuate the transformer arrangement for time-dependent limitation of power consumption from the power grid according to a current/time profile, the current/time profile being deduced from a time-based trip profile of the circuit protection arrangement.

At least one embodiment of the present invention also relates to an X-ray imaging apparatus, comprising:

the power supply apparatus of an embodiment.

At least one embodiment of the present invention also relates to the X-ray imaging apparatus of an embodiment, further comprising:

a further transformer apparatus, operated by the DC output voltage, to generate an operating voltage of an X-ray tube of the X-ray imaging apparatus.

At least one embodiment of the present invention also relates to a method for operating a power supply apparatus for a medical X-ray imaging apparatus, the power supply apparatus including at least one grid connection device, to connect to a power grid providing an AC input voltage, including at least one circuit protection arrangement configured to not trip below a safety current; an actively actuatable transformer arrangement to transform the AC input voltage into a DC output voltage as a supply voltage for the X-ray imaging apparatus; an electrical energy storage system; and a controller to actuate the transformer arrangement to limit power consumption from the electric power grid as a function of the safety current and to make up for a deficit in power requirement for the X-ray imaging apparatus from the energy storage system, the method comprising:

actuating, via the controller, the transformer arrangement for time-dependent limitation of power consumption from the power grid according to a current/time profile, the current/time profile being deduced from a time-based trip profile of the circuit protection arrangement.

BRIEF DESCRIPTION OF THE DRAWINGS

Further advantages and details of the present invention are revealed by the example embodiments described below and with reference to the drawings, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A conventional power supply apparatus is assumed, the actively actuatable transformer arrangement of which serves in particular not only in at least interim rectification of AC input voltage from the electric power grid, to provide a DC output voltage as supply voltage, but may also serve in power factor correction (PFC). The control apparatus is accordingly particularly advantageously configured to actuate the transformer arrangement for power factor correction and/or for automatic control of the transformer arrangement with regard to a default voltage for the DC output voltage.

Such underlying automatic control is then overlaid with a current/time profile, which may be saved in the control apparatus or converted by components, this ultimately describing in time-dependent manner a limiting current drawable from the power grid. This means that a safety current, and therefore a guaranteed minimum holding current, which can be drawn from the power grid for any desired time without the circuit protection arrangement tripping, is no longer used but rather a time-variable limiting current is used which is obtained in accordance with a tripping profile of the circuit protection arrangement.

At least one embodiment of the present invention ultimately combines two insights. On the one hand, common circuit protection arrangements, which may comprise circuit protections for example in the form of a miniature circuit-breaker, have different mechanisms which, when viewed together, define a time-related tripping profile for average current (in particular RMS current) in the power grid through the circuit protection arrangement. Such a first mechanism may be a magnetic current protection mechanism, which trips if a specific, fixed trip current, which is generally markedly higher than the safety current, is exceeded. The second mechanism may be a thermal mechanism which is intended to provide protection against overheating and whose current through the circuit protection arrangement, needed for tripping purposes, decreases over time and in particular approximates to the safety current, optionally taking account of a safety margin.

It should here be noted that these trip characteristics of the different mechanisms are of course generally determined by tolerance ranges, wherein for safety's sake the lower limit of the tolerance range, i.e. the lowest possible trip current, may be considered to be the trip profile. From the time perspective, the trip profile for the circuit protection arrangement thus takes the form of the possibility, for a given period, for example a few seconds, of drawing a markedly higher grid current from the power grid than would be possible as the nominal current according to the safety current. For conventional, known circuit protection arrangements in Germany, the safety current conventionally amounts in single-phase grids to 16 A, as already also indicated in the cited prior art.

By analyzing the circuit protection arrangement, however, it is clear that, for example in the first five seconds of the heavy loading of the power grid, in particular loading exceeding a threshold value, it is wholly possible to draw from the power grid a multiple of, for example up to five times, the safety current, without tripping the circuit protection arrangement. The second insight of the present invention, on the other hand, is that in X-ray imaging apparatus peak powers are mostly only required for really short periods, in particular when X-ray pulses are to be output.

If the actual time-related trip profile of the circuit protection arrangement is thus considered in relation to the short peak power timescales in X-ray imaging apparatus, the described time window in which higher grid currents can be drawn from the power grid without tripping the circuit protection arrangement can be used to increase the energy that can be drawn overall from the power grid. In other words, the current/time profile for low time values may describe a limit current exceeding the safety current, in particular by at least two times, and/or at least approximate to a limit current described by the safety current for higher time values. In this case, it goes without saying that it is conceivable to make the fullest possible utilization of the trip profile, depending on how it is viewed, but it is also conceivable for the current/time profile for each point in time and/or each time interval to describe a grid current which is lower by a percentage safety margin than a trip current of the trip profile at the relevant point in time.

In general terms, the current/time profile thus substantially provides limit current values for different points in time/time intervals which allow the circuit protection arrangement temporarily to exceed the safety current, so allowing a greater amount of power and thus energy to be drawn from the power grid for relatively short periods of time. Limit value utilization of the trip characteristic of the circuit protection arrangement therefore yields added energy value, which above all favorably affects the dimensioning of the energy storage system with regard to cost, weight and bulk, in particular as far as the use of capacitor energy storage systems (electrolyte capacitors or supercapacitors) is concerned. This means that, for the purposes of the present invention, it is particularly advantageous for the energy storage system to be a capacitor, since the short-term gains in energy from the power grid pay off particularly well in this case and are particularly noticeable in terms of configuration, and may in particular lead to major savings with regard to dimensioning (capacity, size etc.). An output-side capacitor of the transformer arrangement is particularly advantageously used as the energy storage system.

In other words, at least one embodiment of the present invention provides automatic control of a transformer apparatus according to a predeterminable current/time characteristic (the current/time profile) for limit value avoidance of tripping a circuit protection arrangement in the power grid, enabling minimum dimensioning of capacitor/energy storage systems. It is particularly advantageously possible merely to use the output-side capacitor of the transformer arrangement as energy storage system.

It should be noted at this point that the power supply apparatus according to the invention can also be used in other applications, therefore consumer apparatus, in which the power requirements tend towards short-term peak powers compared with a relatively low base power. Welding equipment may be cited as an example in this respect.

For X-ray imaging apparatus, at least one embodiment of the present invention may be understood as a development of configurations which allow the operation of X-ray imaging apparatus even using normal service connections. It goes without saying, therefore, that this is straightforwardly possible, also in the context of at least one embodiment of the present invention, once the current or power drawn from the power grid has been throttled in such a way by the specific automatic control method that values remain below the trip characteristic of the circuit protection arrangement installed in the building wiring system. This means that the grid connection used by the grid connection device(s) of the power supply apparatus is not overloaded electrically and the power grid-side grid connection does not have to be adapted. It should be highlighted in this respect that in a particularly advantageous configuration of at least one embodiment of the present invention the current/time profile may be adaptable on the user side to various trip profiles, such that it may ultimately be selected to match the planned location for installation of the X-ray imaging apparatus. In other words, any desired current/time profile may conveniently be set.

In general, with at least one embodiment of the present invention the power or energy needed for X-ray capture is drawn only in part from the power grid during the capture process. The difference is made up from the energy storage system, wherein as a result of at least one embodiment of the present invention the installed energy storage system with its energy storage properties may be made smaller due to better utilization of the power grid. With regard to the energy storage system, it should additionally be noted that the dependency of the X-ray imaging apparatus on the internal grid resistance and grid quality also falls, since the energy needed during X-ray capture may be obtained from the internal energy storage system.

In terms of the transformer arrangement, although it is preferable according to at least one embodiment of the invention to use a rectifier, in particular a bridge rectifier, with downstream step-up converter (boost converter), it is essential for a topology to be present in the power supply apparatus in which the current consumption and thus power consumption can be actively limited or influenced with active switching elements.

It should additionally be noted at this point that the at least one further transformer apparatus, which for example transforms the DC output voltage, which may lie in the range from 380 to 750 V, into an AC operating voltage of an X-ray emitter and optionally further components of the X-ray imaging apparatus, for example in the range from 40 to 140 kW, may also be connected downstream of the transformer arrangement according to at least one embodiment of the present invention.

In a specific configuration of at least one embodiment of the present invention, provision may be made for the control apparatus to comprise an automatic control unit for providing a control variable, in particular a pulse-width modulation duty factor for actuating a switching element, to the transformer arrangement as a function of at least one first measured variable, in particular comprising the DC output voltage of the voltage converter, and an adaptation unit for preadaptation of at least one of the at least one first measured variables for implementation of the current/time profile. Such an adaptation unit may also be understood as a shaper unit, since it ultimately adapts the profile of the or a first measured variable in such a way that the desired current limitation for the grid current arises through automatic control in the automatic control unit.

It is therefore proposed to adapt a first measured variable, which constitutes an input value of the automatic control, such that the other automatic control strategy and also the specific configuration of the automatic control unit may remain completely unchanged. This is of particular advantage in an analog configuration of the automatic control unit, since the automatic control unit can then remain completely unchanged while the control apparatus nevertheless as a whole enables the desired limitation of power consumption from the power grid. However, the previous components of the automatic control algorithm may also ultimately remain unchanged in the case of digital automatic control, which is implemented for example using an automatic control algorithm, if just one algorithm portion implementing the adaptation unit is added which preadapts the value of the first measured variable according to the current/time profile. The adaptation unit may in this case for example be connected between a measurement apparatus, for example a tap-off point, the first measured variable and the automatic control unit.

A development in this context provides that the power supply apparatus has a measurement apparatus for picking up at least one second measured variable describing the current power consumption from the power grid, in particular the grid current flowing in the transformer arrangement and/or a measurement current describing this, wherein the adaptation unit is configured to evaluate the second measured variable for adaptation of at least one of the at least one first measured variables for implementation of the current/time profile.

It is thus conceivable, for example, to measure the grid current or a measurement current describing this in the transformer arrangement, compare it by analog and/or digital device(s) with the current/time profile and undertake a corresponding modification of the first measured variable specifically to implement the current/time profile in the adaptation unit. A current is here particularly suitable as one of the at least one second measured variables, wherein in addition to in particular the grid current and/or the measured current, a voltage related to the grid current or measured current, for example a DC input voltage into the step-up converter, may also particularly advantageously be used as a further second measured variable.

If a step-up converter is used in a specific example embodiment, this conventionally comprises an inductor, in particular a coil, wherein the grid current flowing therein mainly describes the power consumption from the power grid, in particular together with the corresponding DC input voltage for the step-up converter, i.e. the rectified AC input voltage. It is however preferable here to undertake current measurement downstream of an actuatable switching element of the step-up converter, wherein the switching element is conventionally actuated based upon a pulse-width modulation with high frequency, such that a sufficiently close relationship between the measured current there and the grid current is present in the inductor, in particular as far as the profile is concerned from which an RMS value of the grid current can be derived which is comparable with the limit current of the current/time profile. Other measurement points are, of course, however also conceivable. It may also be possible in example embodiments to measure a power directly as a second measured variable.

At least one second measured variable may conveniently be used which in any event is also included in the automatic control as a further one of the first measured variables. In other words, provision may be made for the automatic control unit likewise to be configured to take account of the second measured variable as a further first measured variable, not adapted by the adaptation unit, in determining the control variable. This applies in particular to the DC input voltage of a step-up converter and the measured current downstream of the actively actuated switching element, once, for the purpose of power factor correction and automatic control to a default voltage as DC output voltage, the DC input voltage for the step-up converter arising downstream of the rectifier is conventionally multiplied by a deviation from the default voltage, in order to derive as control variable a duty factor for pulse-width modulation, wherein instantaneous automatic current control may be preferably undertaken by the switching element based upon the measured current. In such cases, the second measured variable therefore also serves as a further first measured variable and is likewise included in the automatic control.

Somewhat more generally, it may be stated in relation to such configurations that it is particularly advantageous if the first measured variable adaptable by the adaptation unit is the DC output voltage and the at least one second measured variable taken into account for adaptation describes the grid current and/or the AC input voltage (and therefore optionally also the DC input voltage downstream of a rectifier). If the DC output voltage as the first measured variable is modified in such a way that it appears lower, the power consumption from the power grid would be increased by the automatic control, with the reverse being the case with an increase in DC output voltage as the first measured variable, such that the power consumption from the power grid may in this way be particularly easily influenced, in particular by carrying out an addition and/or subtraction operation. The at least one second measured variable conveniently describes the power drawn from the power grid and thus also the current flowing therein, in particular in the circuit protection arrangement, which current may for example be compared with the limit current from the current/time profile. In particular with regard to analog implementation, "shaping" of the DC output voltage as the first measured variable may in this case be implemented in a particularly uncomplicated manner, since the addition or subtraction operation is less complex to implement. Although it is in principle also conceivable to modify other first measured variables, for example the AC input voltage or the DC input voltage, this has however proven more complex, since multiplication operations, as would then be needed, are more difficult to implement and moreover constitute nonlinear interventions.

As already indicated, it is particularly advantageous if, in the case of analog configuration of the automatic control unit, the in particular analog-configured adaptation unit, external to the automatic control unit, is connected upstream, in particular with regard to the first measured variable adaptable thereby, of the automatic control unit. In this way, the automatic control unit does not have to be modified and may, as is known from the prior art, be directly adopted. Specifically in single-phase power grids, the use of analog automatic control units is still common due to their simple and inexpensive implementation, resulting in a further clear advantage provided by at least one embodiment of the present invention.

In this case, the adaptation unit may itself be of analog configuration, for example using logic elements and/or comparators and/or operational amplifiers and/or resistors and/or capacitors. If, for example, a current/time profile is to be implemented, which should, for a first time interval of up to four seconds, permit a first limit current, for example twice to five times the safety current, and, for the remaining time interval after four seconds, fix the safety current as limit current, it is conceivable to use two comparators with different time constants/timing elements. In the case of the second comparator, a time delay may then be provided which ensures that it becomes effective only after the first time interval, in particular therefore after four seconds. These two comparators may both be separately settable, in order to allow adaptation to the corresponding trip profile of a circuit protection arrangement to be used, and therefore to derive the actually used current/time profile from the trip profile. In addition to such a simple example embodiment, it goes without saying that a multistage, analog implementation of more complex current/time profiles is also possible.

However, in the context of at least one embodiment of the present invention it is also feasible for both the automatic control unit and the adaptation unit to be digitally implemented, for example in the form of at least one chip or IC. In this case, ultimately an automatic control algorithm is implemented by the automatic control unit and also the adaptation unit. Such digital automatic control topologies are frequently used in the prior art with high powers and/or three-phase power grids, but are also generally useful.

In addition to the power supply apparatus, at least one embodiment of the present invention also relates to an X-ray imaging apparatus, having a power supply apparatus according to the present invention. All explanations with regard to the power supply apparatus according to at least one embodiment of the invention may be applied analogously to the X-ray imaging apparatus according to at least one embodiment of the invention, such that the advantages which have already been stated can also be obtained therewith.

It is in particular possible, as already mentioned, for the X-ray imaging apparatus to have a further transformer apparatus operated by the DC output voltage, in particular an inverter for generating an operating voltage of an X-ray tube of the X-ray imaging apparatus. In this case, it is feasible both ultimately to generate an operating voltage for all components of the X-ray apparatus and also to provide different operating voltages for different components.

Finally, at least one embodiment of the present invention also relates to a method for operating a power supply apparatus for an in particular medical X-ray imaging apparatus, the power supply apparatus comprising:

a grid connection device(s) for connection to a power grid providing an AC input voltage, which has at least one circuit protection arrangement which does not trip below the safety current, an actively actuatable transformer arrangement, in particular comprising a rectifier and a step-up converter, for transforming the AC input voltage into a DC output voltage as supply voltage for the X-ray imaging apparatus, an electrical energy storage system and a control apparatus for actuating the transformer arrangement to limit power consumption from the electric power grid as a function of the safety current and to make up for a deficit in power requirement for the X-ray imaging apparatus from the energy storage system, which method is distinguished in that the control apparatus actuates the transformer arrangement for time-dependent limitation of power consumption from the power grid according to a current/time profile, in particular related to a grid current flow from the power grid, wherein the current/time profile is deduced from a time-based trip profile of the circuit protection arrangement, which in particular takes account of a thermal circuit protection device(s) tripping in the event of persistent overloading.

All the explanations relating to the power supply apparatus according to at least one embodiment of the invention and to the X-ray imaging apparatus according to at least one embodiment of the invention accordingly also apply to the method according to at least one embodiment of the invention.

Figure 1:
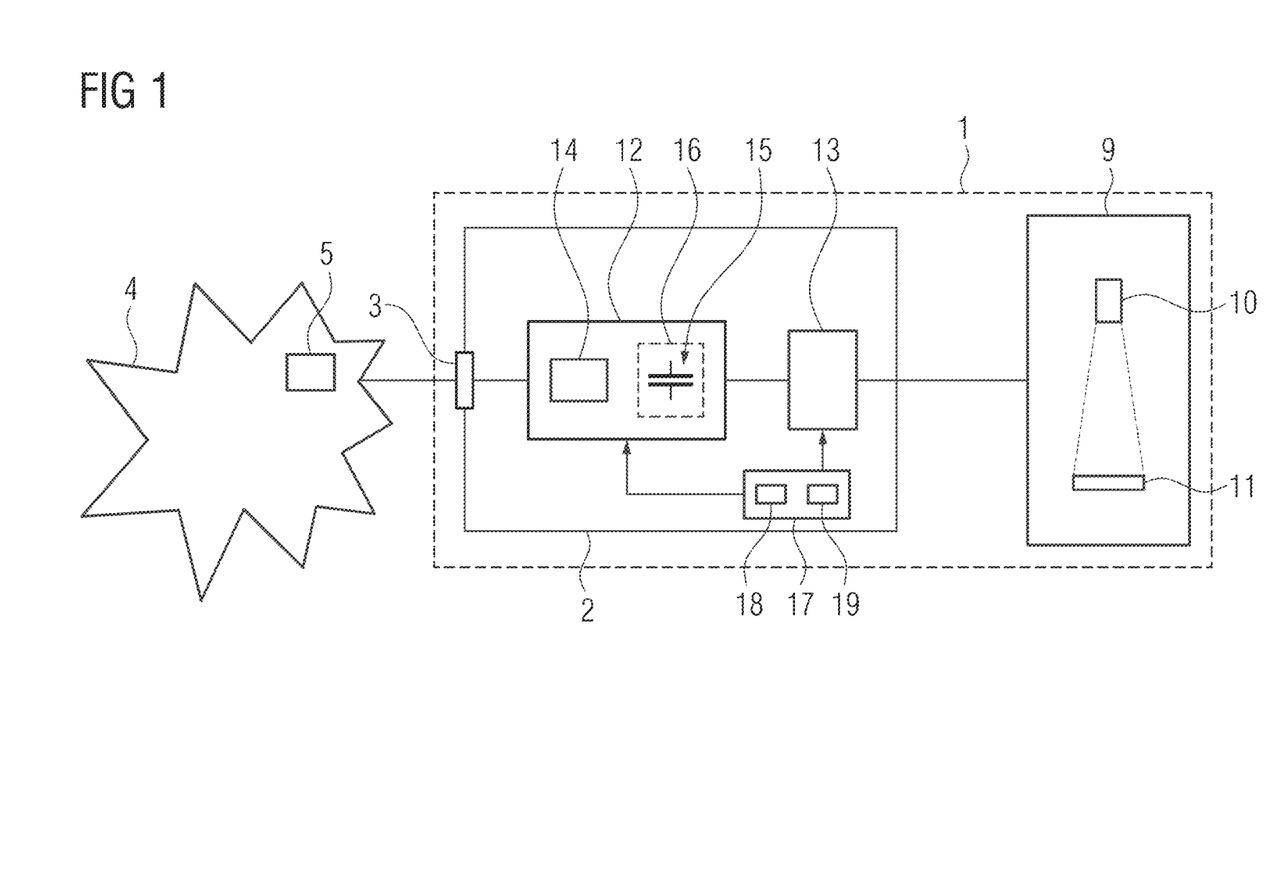
FIG. 1 shows functional components of an X-ray imaging apparatus according to an embodiment of the invention.

FIG. 1 shows a schematic diagram of functional components of an X-ray imaging apparatus 1 according to an embodiment of the invention. This apparatus has a power supply apparatus 2 according to an embodiment of the invention, via the grid connection device(s) 3 of which the X-ray imaging apparatus 1 may be connected to a grid connection of a power grid 4 which is merely indicated here. A circuit protection arrangement 5 is associated with the power grid-side grid connection. For this, on the one hand a guaranteed minimum holding current is known as safety current/nominal current, for which the circuit protection arrangement 5 does not trip even if this safety current is maintained over an extended time. Furthermore, a trip characteristic in the form of a trip profile is known in relation to the circuit protection arrangement 5, which trip profile indicates at what trip currents and after what time tripping occurs.

Figure 2:
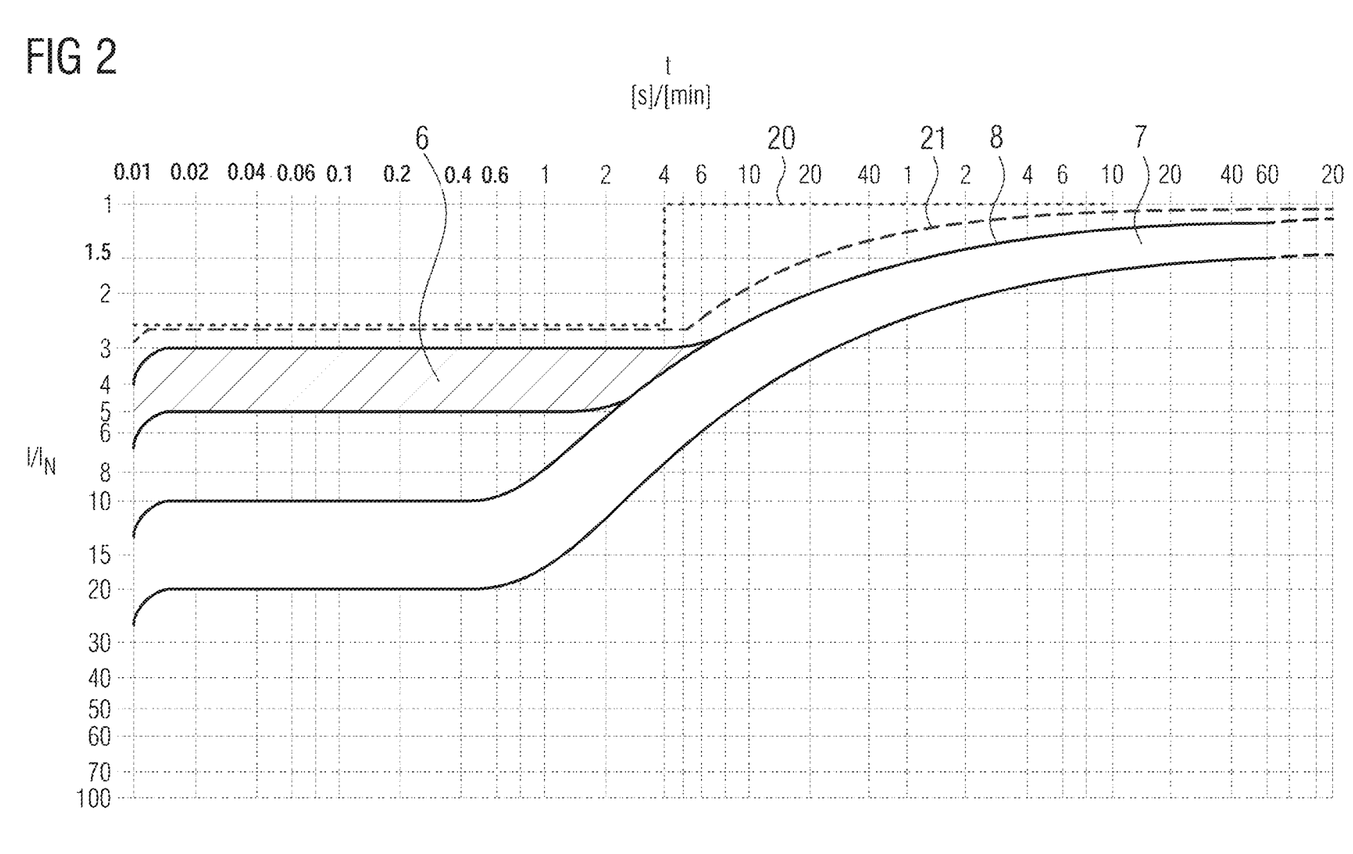
FIG. 2 shows a trip characteristic of a circuit protection arrangement together with current/time profiles derivable therefrom.

Such a trip characteristic is shown by way of example in FIG. 2. The multiple of the safety current IN is plotted downwards, while the horizontal axis plots the time in seconds/minutes, in relation to the trip characteristic illustrated and therefore the trip time after which tripping of the circuit protection arrangement 5 takes place at a given multiple of the safety current.

In the present case, the at least one circuit protection device(s) of the circuit protection arrangement 5 is based on two trip mechanisms, namely a magnetic trip mechanism, the trip characteristic of which is indicated by the tolerance range 6, and a thermal trip mechanism, the trip characteristic of which is indicated by the tolerance range 7. The lower limit of the tolerance ranges 6, 7 relative to the current, i.e. shown at the top in FIG. 2, forms the trip profile 8, which denotes the minimum possible trip current.

Returning to FIG. 1, in addition to the power supply apparatus 2, the X-ray apparatus 1 comprises further components, of which a capture arrangement 9 with an X-ray emitter 10 and an X-ray detector 11 is shown by way of example. In order for the X-ray emitter 10 to be capable of transilluminating an object for X-ray capture, it must generate X-rays at very high powers for a short time. This takes place for example via an X-ray tube. In order to be able to provide the operating voltage for the X-ray emitter 10, the power supply apparatus 2 firstly has a transformer arrangement 12, which provides a DC output voltage, for example in the range from 380 to 750 V, which is forwarded to a further transformer apparatus 13, which provides the AC operating voltage, for example in the range from 40 kW to 140 kW, for the X-ray emitter 10 (and optionally further components of the X-ray imaging apparatus 1).

The transformer arrangement 12 comprises an active transformer topology 14 which is merely indicated here, with at least one switch element actuatable for automatic control of the transformer arrangement 12. In the present case, the transformer arrangement 12 further comprises a capacitor 15, for example an electrolyte capacitor or a supercapacitor, which, as is still to be described, also serves as an energy storage system 16 for the power supply apparatus 2.

Operation of the power supply apparatus 2 is controlled via a control apparatus 17, which here firstly comprises an automatic control unit 18. The automatic control unit 18 automatically controls the transformer arrangement 12 to a default voltage for power factor correction and with regard to DC output voltage. The control apparatus 17 however also includes an adaptation unit 19. The adaptation unit 19 ensures time limitation of the power which can be drawn from the power grid 4 according to a power/time profile, so ensuring that the circuit protection arrangement 5 does not trip but nevertheless at least occasionally allows the safety current to be exceeded and thus at least occasionally allows a larger amount of power and thus energy to be drawn from the power grid 4.

If, for example during X-ray capture, the power required by the X-ray imaging apparatus 1 is greater than the line power drawable at that moment from the power grid 4, the remaining difference is provided from the energy storage system 16.

The current/time profile is in this case derived from the trip profile 8, as likewise shown in FIG. 2. Two current/time profiles 20, 21 are represented schematically therein by way of example. The current/time profile 20 is a simple trip profile which is uncomplicated to implement in analog manner, as will be described below; and which, for a first time interval of up to around four seconds, allows around 2.8 times the safety current, but only the safety current in the time interval after four seconds. The current/time profile 21, however, more closely follows the trip profile 8 with a safety margin. It may for example advantageously be used in digital automatic control.

In any event, higher currents than the safety current may occasionally be drawn from the power grid 4, such that more line power and thus also more energy may occasionally be achieved there, for which reason the capacitor 15 may be smaller in size. Account should be taken of the fact that times when such a peak power is required also tend frequently to be short in X-ray imaging apparatus 1, for example to lie within the time interval shown of up to four seconds, such that significant added energy value is actually obtained.

The control apparatus 17 according to the general description in FIG. 1 thus enables automatic analog or digital PFC and default voltage control, taking account of a predeterminable current/time characteristic for limit value-related trip prevention for the circuit protection arrangement 5, so enabling the capacitors 15/energy storage systems 16 in general used to be of minimal size.

Figure 3:
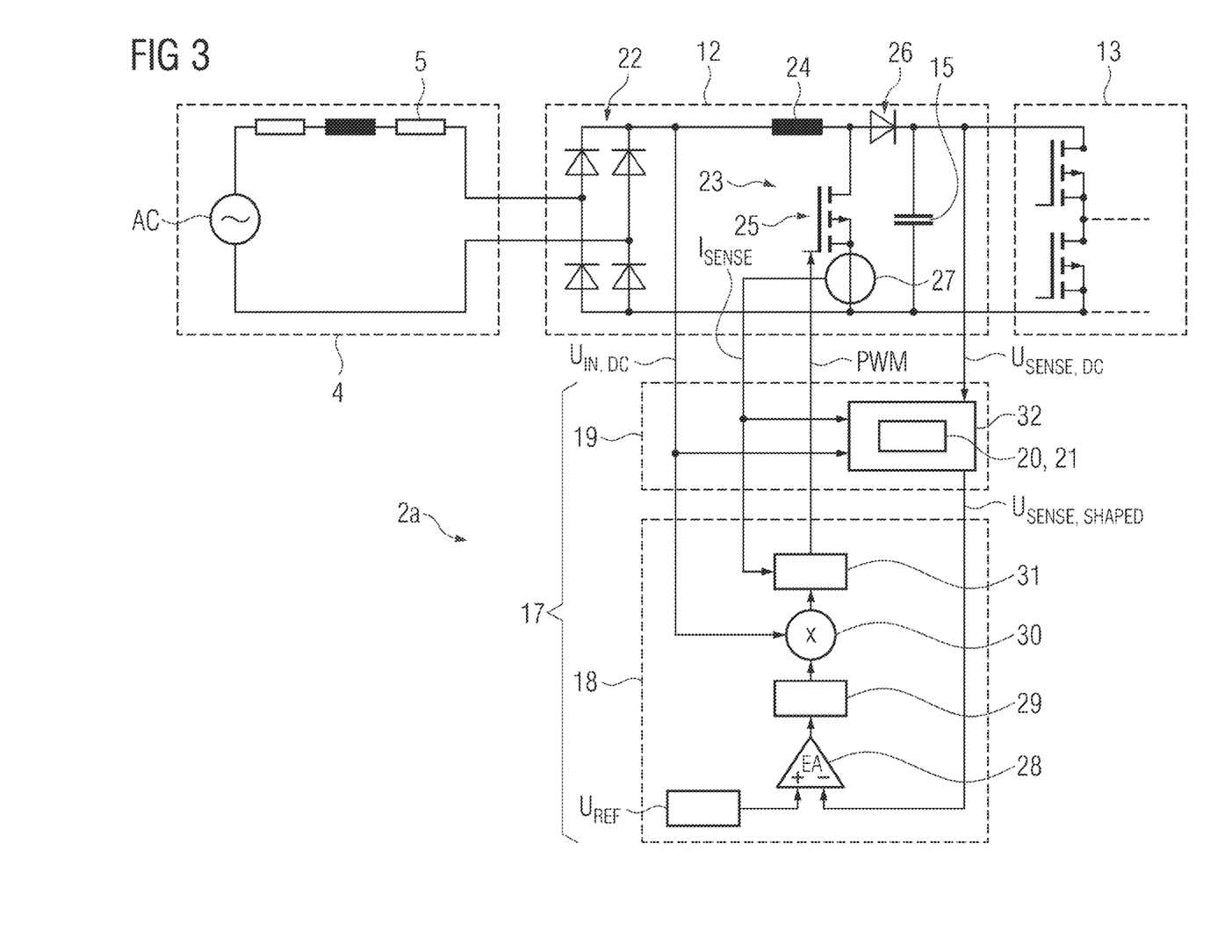
FIG. 3 shows a first specific configuration of a power supply apparatus according to an embodiment of the invention.
Figure 4:
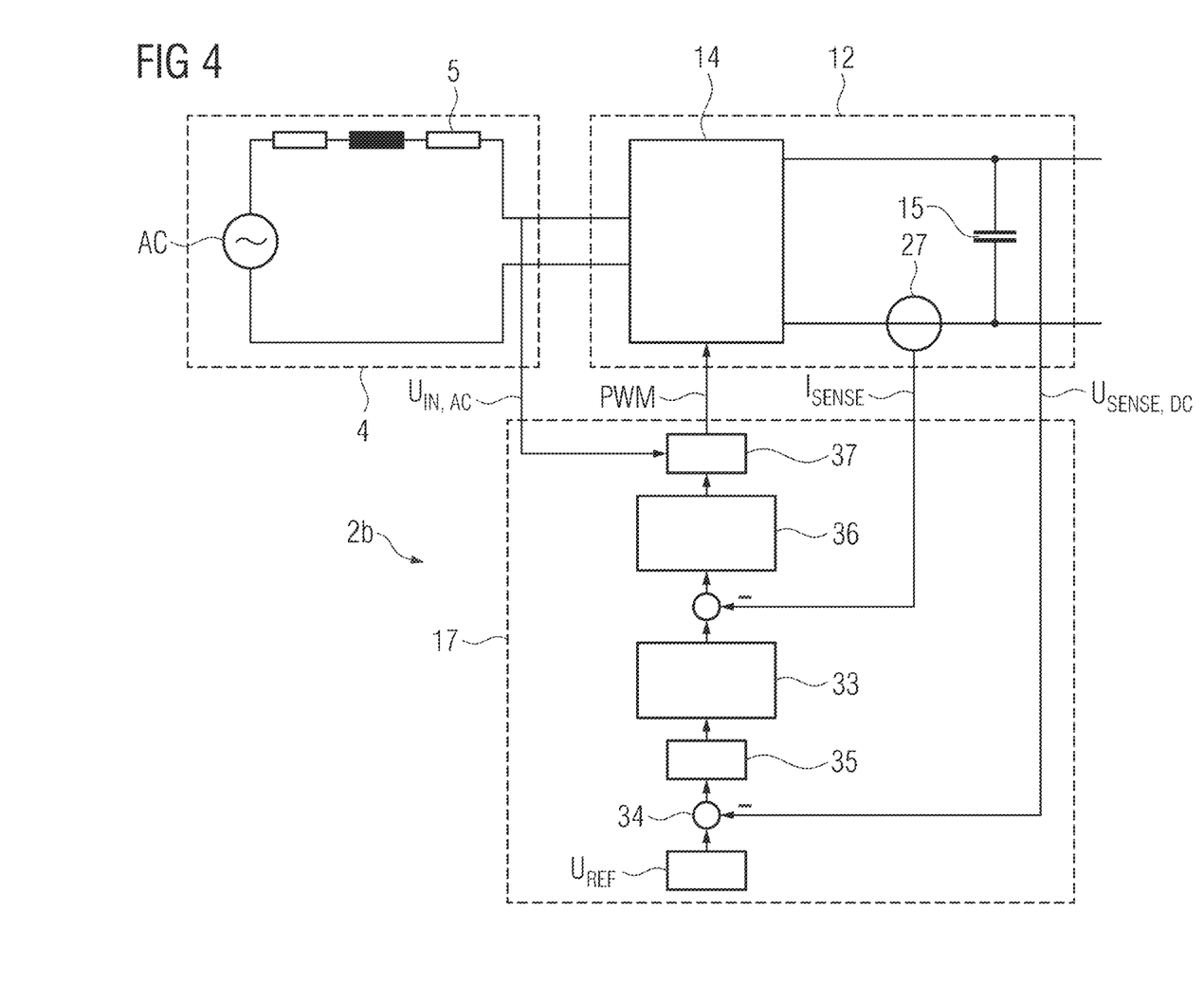
FIG. 4 shows a second specific configuration of a power supply apparatus according to an embodiment of the invention.

FIGS. 3 and 4 show specific example embodiments according to the invention of power supply apparatus 2a, 2b. In the case of FIG. 3, both the automatic control unit 18 and the adaptation unit 19 are analog.

Starting from the power grid 4, the equivalent circuit diagram of which shows not only the circuit protection arrangement 5 but also impedances therein, the transformer arrangement 12 comprises a rectifier 22 and a step-up converter 23 (boost converter). The step-up converter 23 comprises, in addition to an inductor 24, as known in principle, an actuatable switching element 25, a freewheeling diode 26 and the capacitor 15. The grid current through the inductor 24 and the half sine-type DC input voltage present downstream of the rectifier 22 clearly define the power drawn from the power grid 4.

The analog circuit of the automatic control unit 18 is unchanged compared with known systems. The DC output voltage (USENSE,DC), the DC input voltage (UIN,DC) and a measured current (ISENSE) measured using a measurement apparatus 27 are used as first measured variables, according to which automatic control is performed, the control variable forming a duty factor (PWM) at the switching element 25. The measured current is picked up on the ground side via the measurement apparatus 27 downstream of the switching element 25. From this, however, the RMS value of the grid current through the inductor 24 may be straightforwardly derived with sufficient accuracy.

It goes without saying that the automatic control unit 18 described here is purely by way of example. Self-evidently, any prior art automatic control topology that is known in principle can be used here.

In the automatic control topology illustrated purely schematically, the deviation of the DC output voltage from the default voltage (UREF) is firstly determined by an error amplifier 28 and may be prefiltered in an optional filter 29, before multiplication by the DC input voltage proceeds in a multiplier 30. Pulse-width modulation is performed in a block 31, in the present case as instantaneous automatic current control taking account of the measured current.

In order in the present case to limit the power drawn according to the current/time profile 20 or 21, the adaptation unit 19 is connected in the incoming path of the DC output voltage as a first measured variable upstream of the automatic control unit 18, wherein a circuit 32 implementing the current/time profile 20, 21 is used which may conveniently also be of analog configuration. This circuit 32 effects preadaptation of the value of the DC output voltage, wherein in particular an increase will lead to a reduction in the power drawn from the power grid 4 in the context of automatic control by the automatic control unit 18. As input variables, here denoted second measured variables, the measured current and the DC input voltage are used to describe the power drawn from the grid. For analog implementation for example of the current/time profile 20 two comparators may be used, which have different delay elements, such that the second comparator becomes active only after four seconds (end of the time interval) and accordingly the different limit currents in the two time intervals used may accordingly be simply obtained. It goes without saying that more complex configurations are also conceivable, for example if it is necessary to approximate more closely to the current/time profile 21.

The adaptation unit 19 can therefore also be understood as a shaper unit, once the first measured variable has been preadapted to the DC output voltage using second measured variables in such a way that, through automatic control of the automatic control unit 18, without modifying the latter, power consumption is conveniently limited such that the (time-related) trip characteristic 6, 7 of the circuit protection arrangement 5 is taken into account.

FIG. 3 shows another configuration with digital control apparatus 17, wherein for simplicity's sake the active transformer topology 14 is again shown only schematically, also in order to clarify that different configurations of the transformer arrangement 12 can be used. Automatic control is here implemented as an automatic control algorithm, which is supplemented by a step 33 implementing the adaptation unit. Without restriction to this specific example embodiment, the rest of the control algorithm which remains unchanged in turn shows determination of the differences in DC output voltage from the default voltage in an error calculation step 34, a voltage regulator 35, a current regulator 36 and a pulse width modulation step 37.

Although the invention has been illustrated and described in detail with reference to the preferred example embodiment, the invention is not restricted by the disclosed examples and other variations may be derived therefrom by a person skilled in the art without departing from the scope of protection of the invention.

It shall be understood that the embodiments described above are to be recognized as examples. Individual embodiments may be extended by features of other embodiments. In particular, a sequence of the steps of the inventive methods are to be understood as example. The individual steps can also be carried out in a different order or overlap partially or completely in time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A power supply apparatus for an X-ray imaging apparatus, the power supply apparatus comprising:
    at least one grid connection device, to connect to a power grid providing an AC input voltage, including at least one circuit protection arrangement configured to not trip below a safety current;
    an actively actuatable transformer arrangement to transform the AC input voltage into a DC output voltage as a supply voltage for the X-ray imaging apparatus;
    an electrical energy storage system; and
    a control apparatus to actuate the transformer arrangement to limit power consumption from the power grid as a function of the safety current and to make up for a deficiency in a power requirement for the X-ray imaging apparatus from the energy storage system, the control apparatus being configured to actuate the transformer arrangement for time-dependent limitation of power consumption from the power grid according to a current/time profile, the current/time profile being deduced from a time-based trip profile of the circuit protection arrangement.

2. The power supply apparatus of claim 1, wherein the current/time profile, for each at least one of point in time and time interval, describes a grid current relatively lower by a percentage safety margin than a trip current of the time-based trip profile at the at least one of point in time and time interval, and at least one of
    for relatively low time values, describes a limit current exceeding the safety current, and
    for relatively higher time values, at least approximates to a limit current described by the safety current.

3. The power supply apparatus of claim 2, wherein the energy storage system is a capacitor of the transformer arrangement.

4. The power supply apparatus of claim 2, wherein the control apparatus is configured to actuate the transformer arrangement for at least one of power factor correction and automatic control of the transformer arrangement with regard to a default voltage for the DC output voltage.

5. The X-ray imaging apparatus, comprising:
    the power supply apparatus of claim 2.

6. The X-ray imaging apparatus of claim 5, further comprising:
    a further transformer apparatus, operated by the DC output voltage, to generate an operating voltage of an X-ray tube of the X-ray imaging apparatus.

7. The power supply apparatus of claim 1, wherein the energy storage system is a capacitor of the transformer arrangement.

8. The power supply apparatus of claim 7, wherein the capacitor is an output-side capacitor.

9. The power supply apparatus of claim 1, wherein the control apparatus comprises
    an automatic controller to provide a control variable to the transformer arrangement as a function of at least one first measured variable, and
    an adaptation unit to preadapt at least one of the at least one first measured variable for implementation of the current/time profile.

10. The power supply apparatus of claim 9, further comprising:
    a measurement apparatus to pick up at least one second measured variable describing current power consumption from the power grid, wherein the adaptation unit is configured to evaluate the at least one second measured variable for adaptation of at least one of the at least one first measured variable for implementation of the current/time profile.

11. The power supply apparatus of claim 10, wherein the automatic controller is configured to take account of the at least one second measured variable as a further first measured variable, not adapted by the adaptation unit, in determining the control variable.

12. The power supply apparatus of claim 11, wherein the at least one first measured variable adaptable by the adaptation unit is the DC output voltage and the at least one second measured variable taken into account for adaptation describes at least one of a grid current and the AC input voltage.

13. The power supply apparatus of claim 10, wherein the at least one first measured variable adaptable by the adaptation unit is the DC output voltage and the at least one second measured variable taken into account for adaptation describes at least one of a grid current and the AC input voltage.

14. The power supply apparatus of claim 9, wherein, in a case of analog configuration of the automatic controller, the adaptation unit, external to the automatic controller, is connected upstream of the automatic controller.

15. The power supply apparatus of claim 9, wherein the automatic controller provides a control variable, that is a pulse-width modulation duty factor for actuating a switching element, to the transformer arrangement as a function of the at least one first measured variable, the at least one first measured variable including the DC output voltage of a step-up converter.

16. The power supply apparatus of claim 1, wherein the control apparatus is configured to actuate the transformer arrangement for at least one of power factor correction and automatic control of the transformer arrangement with regard to a default voltage for the DC output voltage.

17. The X-ray imaging apparatus, comprising:
the power supply apparatus of claim 1.

18. The X-ray imaging apparatus of claim 17, further comprising:
a further transformer apparatus, operated by the DC output voltage, to generate an operating voltage of an X-ray tube of the X-ray imaging apparatus.

19. The power supply apparatus of claim 1, wherein the actively actuatable transformer arrangement includes a rectifier and a step-up converter.

20. The power supply apparatus of claim 1, wherein the control apparatus is configured to actuate the transformer arrangement for time-dependent limitation of power consumption from the power grid according to the current/time profile, related to a grid current flow from the power grid, the current/time profile being deduced from a time-based trip profile of the circuit protection arrangement which takes account of at least one thermal circuit protection device tripping in an event of persistent overloading.

21. The power supply apparatus of claim 20, wherein the current/time profile, for each at least one of point in time and time interval, describes a grid current relatively lower by a percentage safety margin than a trip current of the time-based trip profile at the at least one of point in time and time interval, and at least one of
for relatively low time values, describes a limit current exceeding the safety current, and
for relatively higher time values, at least approximates to a limit current described by the safety current.

22. A method for operating a power supply apparatus for a medical X-ray imaging apparatus, the power supply apparatus including at least one grid connection device, to connect to a power grid providing an AC input voltage, including at least one circuit protection arrangement configured to not trip below a safety current; an actively actuatable transformer arrangement to transform the AC input voltage into a DC output voltage as a supply voltage for the X-ray imaging apparatus; an electrical energy storage system; and a controller to actuate the transformer arrangement to limit power consumption from the power grid as a function of the safety current and to make up for a deficit in power requirement for the X-ray imaging apparatus from the energy storage system, the method comprising:
actuating, via the controller, the transformer arrangement for time-dependent limitation of power consumption from the power grid according to a current/time profile, the current/time profile being deduced from a time-based trip profile of the circuit protection arrangement.

23. The method of claim 22, wherein the actuating includes actuating the transformer arrangement for time-dependent limitation of power consumption from the power grid according to the current/time profile, related to a grid current flow from the power grid, the current/time profile being deduced from a time-based trip profile of the circuit protection arrangement which takes account of at least one thermal circuit protection device tripping in an event of persistent overloading.

* * * * *